United States Patent [19]

Borrod et al.

[11] Patent Number: 4,738,708
[45] Date of Patent: Apr. 19, 1988

[54] N-SULPHONYL-N-[N'PHOSPHONOME-THYLGLYCYL]AMINE AND DERIVATIVES AS HERBICIDES

[75] Inventors: Guy Borrod; Guy Lacroix, both of Lyons, France

[73] Assignee: Rhone-Poulenc Agrochimie, Lyons, France

[21] Appl. No.: 635,226

[22] Filed: Jul. 27, 1984

[30] Foreign Application Priority Data

Jul. 27, 1983 [FR] France .................................. 83 12620
Feb. 23, 1984 [FR] France .................................. 84 02988

[51] Int. Cl.$^4$ .......................... A01N 57/04; C07F 9/40
[52] U.S. Cl. .................................. 71/87; 260/502.5 F; 558/174
[58] Field of Search ...................... 260/502.5 F; 71/87

[56] References Cited

FOREIGN PATENT DOCUMENTS 2144425 3/1985 United Kingdom ................... 71/87

Primary Examiner—Anton H. Sutto
Attorney, Agent, or Firm—Morgan & Finnegan

[57] ABSTRACT

Herbidical compounds of the formula:

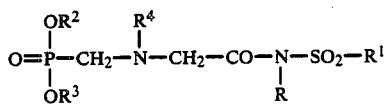

in which $R^1$ denotes an optionally substituted hydrocarbon radical, R denotes the hydrogen atom or has one of the meanings given for $R^1$; $R^2$ and $R^3$ denote the hydrogen atom or are such that $OR^2$ and $OR^3$ are hydrolyzable groups; $R^4$ denotes a hydrogen atom or a hydrogenolyzable group, and the agriculturally acceptable salts of these compounds.

21 Claims, No Drawings

N-SULPHONYL-N-[N'PHOSPHONOMETHYL-GLYCYL]AMINE AND DERIVATIVES AS HERBICIDES

The present invention relates to new herbicides belonging to the chemical family of sulphonamides containing an aminomethylphosphonic group, as well as intermediate products for the preparation of these herbicides, processes for preparing these various products and the use of the said herbicides in agriculture.

Numerous products containing an aminomethylphosphonic group and having herbicidal properties are known, particularly in French Pat. Nos. 2,129,327, 2,281,375, 2,251,569, 2,413,398, 2,463,149, European Pat. Nos. 53,871, 54,382, 73,574, U.S. Pat. Nos. 3,160,632, 3,455,675, 3,868,407, 4,388,103, 4,397,676, British Pat. No. 2,090,596, World patent WO No. 83/03,608, and Belgian Pat. Nos. 894,244, 894,245, 894,590, 894,591, 894,592, 894,593, 894,594 and 894,595.

Numerous intermediate products in the preparation of such products are also known, particularly in European Pat. Nos. 81,459, 97,522, 55,695, French Pat. No. 2,193,830, and U.S. Pat. Nos. 3,835,000 and 4,422,982.

Nevertheless, it is always desirable to extend the range of available herbicides, in order to respond better to the needs of agronomists and to extend the range of intermediates which make it possible to obtain herbicides, and to develop new synthetic routes to herbicidal compounds.

An objective of the present invention is, moreover, to provide herbicides having a high and fast activity.

Another objective of the present invention is to provide herbicides which have low persistence and are easily biodegradable.

Another objective of the present invention is to provide post-emergence herbicides with a wide spectrum of activity, a descending systemic action, and which are, if appropriate, selective for some crops.

Another objective of the present invention is to provide intermediate products and processes for use in preparing herbicides containing an aminomethylphosphonic group.

Another objective of the invention is to provide a very simple and improved process for preparing herbicides which employs relatively simple reactants, particularly glycine and its simple derivatives.

Other objectives and advantages of the invention will appear in the course of the following description.

The compounds according to the invention, which may be employed particularly either as herbicides or as chemical intermediates, are compounds of the formula:

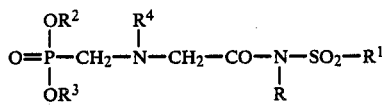

in which: $R^1$ denotes a hydrocarbon radical, particularly alkyl, aryl (e.g. phenyl) or cycloalkyl (e.g. cyclohexane), these various radicals being optionally substituted by substituents, such as halogen atoms and phenyl cyano, alkoxy (preferably $C_1$ to $C_4$), and alkylcarboxylate (preferably $C_1$ to $C_5$) groups, $R^1$ generally contains from 1 to 18 carbon atoms, preferably from 1 to 7 carbon atoms, and more especially from 3 to 7 carbon atoms in the case of a cycloalkyl group, a preferred $R^1$ group being an alkyl radical containing 1 to 4 carbon atoms, optionally substituted by halogen, especially chlorine or fluorine e.g. trifluoromethyl; R denotes the hydrogen atom or has one of the meanings given for $R^1$, preferably an alkyl group of 1 to 6 carbon atoms more preferably of 1 to 4 carbon atoms said alkyl optionally substituted by halogen, especially chlorine or fluorine; $R^2$ and $R^3$ each represent the hydrogen atom or are such that $OR^2$ and $OR^3$ are hydrolyzable groups, $R^2$ and $R^3$ in the formula may be in particular an aryl (e.g. phenyl) radical or cycloalkyl or, preferably, an alkyl radical, optionally substituted, particularly by the substituents described above for $R^1$ whereby $R^2$ and $R^3$ in general each contain from 1 to 12 carbon atoms and preferably from 1 to 8 carbon atoms; $R^4$ denotes a hydrogen atom or a hydrogenolyzable group $R^8$; in particular $R^8$ may be a radical of the formula $Ar(R^5)(R^6)C-$ in which Ar is an aromatic group, preferably phenyl, and $R^5$ and $R^6$ are each selected from hydrogen atoms or an Ar radical or an alkyl group preferably containing up to 6 carbon atoms.

The compounds of the invention include the agriculturally acceptable salts of the compounds defined by the foregoing formula (I). Salts of compounds of formula I can be formed by the P—OH groups and also by the nitrogen atom to which the group $R^4$ is attached, which can be converted to an ammonium group.

Agriculturally acceptable salts include the alkali metal (e.g. sodium or potassium), alkaline earth metal, ammonium (e.g. the ammonium salts and primary, secondary, tertiary and quaternary ammonium salts) and sulphonium salts. Other salts may include acid addition salts, for example, those formed with hydrochloric acid, sulphuric acid, phosphoric acid and other acids having a pH less than 2.5.

Among the compounds of general formula (I) which are of particular interest owing to their herbicidal activity are the compounds of the formula (I) wherein $R^2$, $R^3$ and $R^4$ are hydrogen atoms, R and $R^1$ are alkyl radicals containing from 1 to 4 carbon atoms, optionally substituted (particularly by halogen), and salts of these compounds.

The invention also relates to intermediate compounds of the formula:

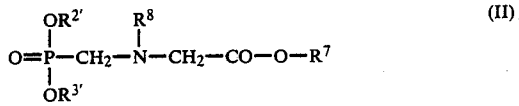

in which $R^{2'}$ and $R^{3'}$ have the meanings given above for $R^2$ and $R^3$ in formula (I), with the exception that $R^{2'}$ and $R^{3'}$ are not hydrogen and $R^{2'}$ and $R^{3'}$ are such that $OR^{2'}$ and $OR^{3'}$ are hydrolyzable groups, $R^{2'}$ and $R^{3'}$ being preferably alkyl radicals most preferably of 1 to 4 carbon atoms; $R^8$ has the meaning already given for formula (I); $R^7$ has the same meaning given for $R^{2'}$ and $R^{3'}$.

In the preceding formulae, Ar denotes an aromatic group, preferably aryl and more especially phenyl; this radical Ar may, if desired, carry one or more substituents which are not detrimental to the reactions involved in the process (e.g. alkyl, alkoxy, nitro, halogens and others, each alkyl and alkoxy substituent having up to 6 carbon atoms.

Illustrative of the radicals $R^8$ that may be mentioned are benzyl, 1-phenylethyl, 1-phenylpropyl, naphthylmethyl, 1-naphthylethyl, 1-naphthylpropyl, diphenylethyl, and trityl (=triphenylmethyl) radicals.

With regard to intermediate compounds and methods for synthesis, reference is made to a copending U.S. patent application filed contemporaneously herewith in the name of Guy Lacroix entitled "Esters of the N-Phosphonomethylglycine Family and Their Use in Preparing Herbicides", which claims Convention priority to French application No. 84-02988 filed Feb. 23, 1984 and French application No. 83-12620 filed July 27, 1983. That application is incorporated herein by reference.

The compounds of the formula (I) in which R is other than the hydrogen atom are most conveniently prepared from compounds of the formula:

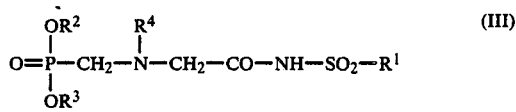
(III)

by reaction with an ester of the formula X—R, R having the meaning given for R in the formula (I), except that R is not hydrogen, and XH being a protonic acid (inorganic or organic) preferably a strong inorganic acid; X is advantageously a chlorine, bromine, or iodine atom or a sulphate group. Preferably X—R is an alkyl halide. This reaction is advantageously carried out in a solvent, in the presence of an alkaline agent, at a temperature of between $-10°$ and $+100°$ C. The reactant of the formula (III) which is employed is preferably such that $R^2$, $R^3$ and $R^4$ are other than hydrogen atoms; it would also be possible to employ products of the formula (III) in which $R^2$ and $R^3$ are H but, in that case, a significant part of X—R would be used up in esterifying the OH groups of the product of formula (III).

Compounds of formula (III) in which $R^2$, $R^3$ and $R^4$ are other than hydrogen atoms are generally prepared by reacting compounds generally corresponding to the formula (II) except that $R^7$ therein is H, with a sulphonyl isothiocyanate of the formula $R^1$—$SO_2$—N=C=S, preferably in a solvent and in the presence of an alkaline agent, preferably a tertiary amine. The reaction is advantageously carried out between 10° and 120° C.

Products of formula (II) in which $R^{2'}$, $R^{3'}$ and $R^8$ are as hereinabove defined and $R^7$ is replaced by H are generally prepared by hydrolysis of products of formula (II) in which $R^{2'}$, $R^{3'}$, $R^8$ and $R^7$ are as hereinabove defined. In practice, this hydrolysis converts the group —$OR^7$ to a hydroxy group by a saponification which in general employs a molar quantity of an alkaline agent which is substantially equal to the molar quantity of the product of formula (II).

Products of formula (II) in which $R^{2'}$, $R^{3'}$, $R^8$ and $R^7$ are hereinabove defined (all other than H) are conveniently prepared by a reaction of (i) the phosphite (or phosphonic ester) of the formula:

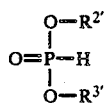
(IV)

with (ii) formaldehyde and with (iii) an N-substituted derivative of glycine of the formula $R^8$—NH—CH$_2$—CO—O—$R^7$, wherein the substituent on the nitrogen atom is a hydrogenolyzable substituent.

The reaction is generally carried out between 0° and 100° C., preferably between 20° and 90° C., by mixing the reactants. Although a large excess (3/1 to ⅓ in molar ratios) of one of the reactants relative to another is possible, in practice it is more advantageous to approach stoichiometry as closely as possible and not to depart by more than 20 mole % from this stoichiometry. It is indeed one of the major advantages not to require an excess of one of the reactants relative to the others. Another advantage lies in the good yields which are obtained in the preparation of the compounds of formula (II).

Formaldehyde is employed in any of its conveniently accessible forms. According to a most widely used method it is employed in the form of an aqueous solution of a concentration of between 1% and saturation, preferably of 30 to 40%.

The reaction may be carried out in the presence of an inert solvent, but in general such a solvent is unnecessary and it is indeed another advantage that a solvent is not required for the preparation of the compounds of formula (II), except for water in the aqueous solution of formaldehyde (formalin), according to the preferred method. The reaction product is separated by any means known per se.

The compounds of formula (II) may be converted into certain herbicidal products (some of which may be known) of the formula:

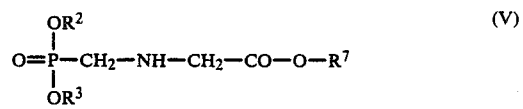
(V)

by simple hyrogenolysis of the $R^8$ group. In the majority of cases this is a debenzylation. Advantageously it is carried out in an aqueous or alcoholic medium at ambient or elevated temperature, at atmospheric pressure or above.

The catalyst employed may be the usual catalysts for hydrogenolysis of the $R^8$ radicals in question. As suitable catalysts there may be mentioned palladium, platinum and Raney nickel. This catalyst may be employed with or without an inert carrier. It is also possible to employ the above-mentioned metals, particularly palladium and platinum, in the form of salts, hydroxides, or oxides, which are converted to the corresponding metal by the action of hydrogen. As a preferred debenzylation catalyst, use is made of palladium-based catalysts such as palladium on charcoal or palladium on barium sulphate or palladium hydroxide on charcoal. At the end of the reaction the catalyst may be separated by filtration and the filtrate evaporated; the product of formula (V) is thus obtained in a substantially pure state. A major advantage of the invention lies in the fact that the reaction time for this debenzylation is relatively short which makes it possible to employ smaller quantities of catalyst.

When it is desired to prepare non-esterified forms of herbicides, such as, e.g., N-phosphono-methylglycine itself, it is possible to hydrolyze completely or partly the product of formula (V) in a known manner, e.g. by heating with an aqueous solution of an acidic or alkaline agent, particularly a hydroxide or carbonate of alkali metal or alkaline earth metal, or a strong inorganic or organic acid, such as hydrochloric, sulphuric, phosphoric, perchloric or arylsulphonic acids. This hydrolysis may also be accompanied by a salt formation (in order to form agriculturally acceptable salts) or a conversion into other herbicidal derivatives.

The compounds according to the invention of the formula:

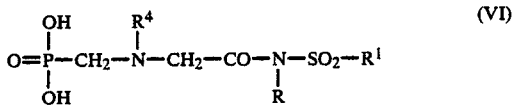

are most conveniently prepared by dealkylation (or transesterification) of the products of formula (I) in which $R^2$ and $R^3$ are other than hydrogen atoms to convert the groups $OR^2$ and $OR^3$ to hydroxy groups. This dealkylation is advantageously carried out by the action of a hydrogen halide acid in a protic polar organic solvent medium, such as e.g. the lower aliphatic carboxylic acids.

The compounds of the formula:

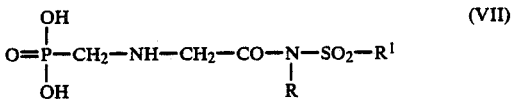

are most conveniently prepared by hydrogenolysis of the $R^8$ group of the products of formula (VI) in which $R^4$ is $R^8$; the hydrogenolysis conditions are in general similar to those described earlier for the preparation of the compounds of the formula (V).

According to the present invention, there is provided another process for preparing certain compounds within formula (I) in which R, $R^1$, $R^2$, $R^3$ and $R^4$ are other than hydrogen atoms i.e. compounds of the formula:

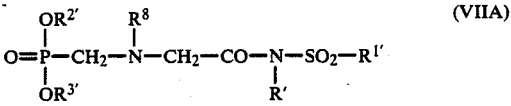

wherein $R^{2'}$, $R^{3'}$, and $R^8$ are as hereinabove defined and wherein R' and $R^{1'}$ are as hereinabove defined for R and $R^1$, respectively except that R' and $R^1$ do not represent hydrogen. Said process comprises reacting a sulphonamide of formula R'—NH—SO$_2$—$R^{1'}$ with a mixed anhydride of the formula:

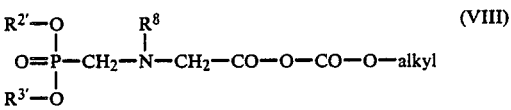

Wherein "alkyl" of the formula is preferably an alkyl group of 1 to 4 carbon atoms. The anhydride of formula VIII is itself obtained by reaction of a compound of the formula:

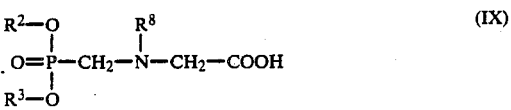

which is preferably in the form of a salt, with an alkyl chloroformate of the formula Cl—CO—O—alkyl wherein alkyl is of 1 to 4 carbon atoms. The compound of formula (IX) is advantageously employed in the form of an ammonium salt and especially in the form of a salt of a tertiary amine, such as triethylamine. The reaction is advantageously carried out at a temperature of between −30° and +10° C. in the presence of a solvent; if use is made of a solvent in which the salts formed during the reaction are insoluble, it then suffices to separate the reaction product by filtration. It is thus possible to employ ethers and esters as solvents, particularly tetrahydrofuran and ethyl acetate.

The compound of formula (IX) can be prepared by hydrolysis of a compound of formula (II), preferably in the presence of an alkaline agent in a quantity of at least about stoichimetric.

The reaction of a mixed anhydride of the type described in formula (VIII) with a sulphonamide of the general formula $R^1$—SO$_2$—NH—R is advantageously carried out in a water/organic solvent two-phase medium in the presence of an alkaline agent and a phase transfer catalyst preferably a quaternary ammonium salt. The temperature is generally between 0° and 50° C. As phase transfer catalysts (generally employed in a concentration of 0.1 to 10% by weight relative to the mixed anhydride) there may be mentioned the quaternary ammonium salts of a strong acid, such as tetraalkylammonium or trialkylaralkylammonium halides or sulphates. The alkaline agent employed is advantageously an alkali metal hydroxide or carbonate or an alkaline earth metal ammonium hydroxide or carbonate, preferably an alkali metal hydroxide.

An illustration of a suitable water immiscible organic solvent is methylene chloride.

As mentioned earlier the compounds according to the invention, especially those of formula (I) may be in the form of agriculturally acceptable salts. Such salts may be prepared by methods known in the art. Salts may thus, if appropriate, form or be formed with the components of the compositions or formulations containing the active ingredient according to the invention and which are employed in practice and the nature of which will be described hereinafter.

The following examples, which are given without implying a restriction, illustrate the invention and show how it can be employed.

Examples 1 to 11 illustrate the synthesis and the physical properties of herbicidal compounds and chemical intermediates according to the invention. The melting points shown correspond generally to a phenomenon of melting with decomposition. When spectral characteristics are given, these are either infrared (IR) absorption bands expressed in cm-1 or proton chemical shifts in nuclear magnetic resonance (NMR); in this latter case the shifts are expressed in ppm (parts per million) and the measurements are carried out in deuterated chloroform in the presence of tetramethylsilane as a reference.

Example 12 illustrates the application of products according to the invention during post-emergence (the terms post-shoot and post-emergence are synonymous).

EXAMPLE 1

The starting material employed is N-benzyl-N-(diethylphosphonomethyl)glycine of the formula:

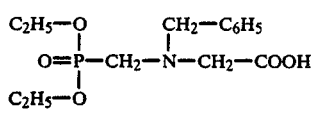 (X)

the preparation of which is described in Example 7.

The product of formula (X) (56.3 g) is dissolved in acetonitrile (200 ml). Triethylamine (0.1 ml) is added and methylsulphonyl isothiocyanate (CH₃—SO₂—NCS) (24.59 g) is added dropwise. The COS released is trapped in a methanolic solution of sodium hydroxide. The temperature rises from 20° to 35° C. After the addition, the mixture is boiled under reflux for 1 hour and then concentrated under reduced pressure.

An oily product of the formula:

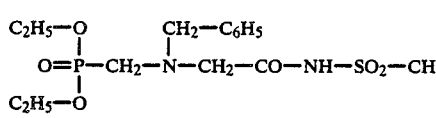 (XI)

(70.5 g) is obtained. This compound is named N-methanesulphonyl-N-[N-benzyl-N-diethylphosphonomethylglycyl]amine.

EXAMPLE 2

(Compound No. 1 of Table I)

The product of formula (XI) (23.5 g) is dissolved in dimethylformamide (100 ml). Sodium hydride (80% purity; 1.8 g) is added to the reactor, which is maintained at 25° C. under a nitrogen atmosphere. After the addition the reaction is allowed to proceed for 30 minutes at 20° C., then methyl iodide (9.9 g) is added. The temperature rises from 21° to 24° C. Heating to 70° is applied for half an hour. The solvent is evaporated off, CH₂Cl₂ (200 ml) is added; the material is washed with aqueous carbonate solution and then water, dried and concentrated. An oily product of the formula:

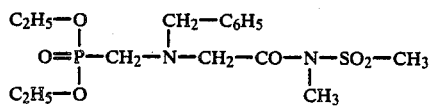 (XII)

(16 g) is obtained.

EXAMPLE 3

(Compound No. 19 of Table I)

Anhydrous HBr (50 g) is dissolved in acetic acid (100 ml) at 15° C. and the temperature is maintained with the aid of an ice water bath. A solution containing the product of formula (XII) (45 g) and acetic acid (45 ml) is added. Reaction is allowed to proceed for 30 hours at 20° C. The material is concentrated, dissolved in methanol, precipitated with propylene oxide, filtered, washed with methanol and dried. The compound of the formula:

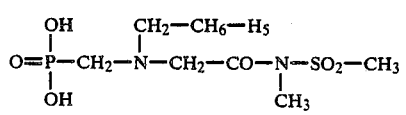 (XIII)

(36 g; 93% yield) is obtained. This product is a white powder which melts at 205° C. The compound is named N-methyl-N-methanesulphonyl-N-[N-benzyl-N-phosphonomethylglycyl] amine.

EXAMPLE 4

(Compound No. 37 of Table I)

Palladium catalyst deposited on carbon black (10% w/w Pd) (1 g) is mixed with concentrated HCl (20 ml) and methanol (150 ml). The product of formula (XIII) (8.4 g) is dissolved. A stream of hydrogen is passed and stopped when the temperature has come back down from 24° to 21° C. The mixture is filtered and the filtrate concentrated. The concentrate is dissolved in methanol (50 ml). Propylene oxide (2 ml) is added, causing a salting out. The precipitate is filtered off and washed with acetone; the compound of the formula:

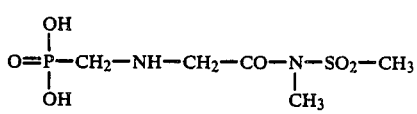 (XIV)

(4.8 g) is obtained, having the name N-methyl-N-methanesulphonyl-N-[N-phosphonomethylglycyl]amine.

EXAMPLE 5

This Example illustrates the preparation of an ester intermediate compound, Methyl-N-benzyl-N-(diethylphosphonomethyl)glycinate.

An aqueous formaldehyde solution (30% by weight) (1,466 g; 14.66 moles) is poured, with stirring, at ambient temperature, over 1 h 30 min, into a mixture of ethyl N-benzylglycinate (2,830 g; 14.66 moles) and diethyl phosphite [C₂H₅O)₂P(0)H] (2,028 g; 14.17 moles). During the pouring the temperature rises up to 41° C. The mixture is heated at 90° C. for 1 h 30 min and then cooled.

To extract the reaction product, CH₂Cl₂ (7 l is added, and the mixture is washed with water (3×6 l). The solvent is removed. A light-brown oil (4,647 g) with a refractive index $n_D^{20}$ of 1.491 is thus obtained. The yield is 92.4%. The product obtained has the formula:

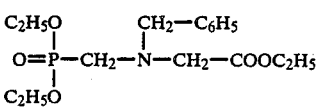 (XV)

EXAMPLE 6

The procedure in Example 5 is followed except that the diethylphosphite is replaced with dimethyl phosphite (also called methyl phosphonate) of the formula (CH₃O)₂P(0)H.

The ester intermediate compound of the formula:

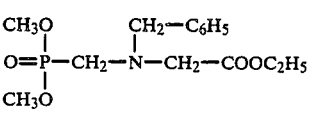 (XVI)

is obtained in 87% yield; its refractive index $n_D^{20}$ is 1.499.

EXAMPLE 7

An aqueous solution containing 5% by weight of sodium hydroxide (6.8 l) is poured at 40° C., over 1½ h, into the compound of formula (XV) (2,915 g). The mixture is then heated at 80° C. for 1½ h, cooled and washed with $CH_2Cl_2$ (4 l). The aqueous solution is acidified to pH 2 with 10 N hydrochloric acid (800 ml). The product separates from the aqueous layer in the form of an oil which is extracted with $CH_2Cl_2$ (5 l). The methylene chloride solution is washed with water (2×2.5 l). It is evaporated to dryness and the intermediate/starting material of formula (X) (2,012 g; 75% yield), which crystallizes on storage (m.p.: 37° C.) is thus obtained.

EXAMPLE 8

The procedure is as in Example 7, the product of formula (XVI) being employed in place of the compound of formula (XV) as starting material. The intermediate compound of formula:

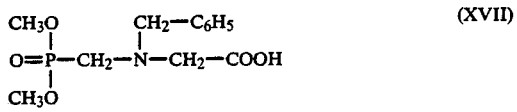

which melts at 73.8° C., is thus obtained in 36% yield.

EXAMPLE 9

A solution of the compound of formula (XV) (68.6 g) in methanol (150 ml) is charged into a 500 ml reactor. A paste made with water (10 ml) and activated charcoal containing 10% by weight of palladium (9 g) is added. The atmosphere is purged with nitrogen and then hydrogen is circulated for 5 h at 20° C. The material is filtered, the filtrate is evaporated and the product of the formula:

$$(C_2H_5O)_2P(O)—CH_2—NH—CH_2—COOC_2H_5 \quad (XVIII)$$

(49 g; 97% yield) is thus obtained in the form of a liquid with a refractive index $n_D^{20}$ of 1.451. This compound of formula (XVIII) (12.7 g) is dissolved in an aqueous solution (50 ml) containing 20% by weight of hydrochloric acid. The solution is boiled under reflux for 20 h. It is concentrated under reduced pressure, and the residue washed with methanol. After drying, N-(phosphonomethyl)-glycine (6.5 g; 77% yield) is obtained.

EXAMPLE 10

The compound of formula (X) (10 g) is dissolved in methanol (50 ml) in a 250 ml reactor. The catalyst paste employed in Example 9 (0.3 g) is added. The atmosphere is purged with nitrogen, and hydrogen is then circulated for 2 h at ambient temperature (20° to 25° C.). The material is filtered, the filtrate evaporated and the product of the formula $(C_2H_5O)_2P(O)—CH_2—NH—CH_2—COOH$ (7.5 g; 100% yield) is obtained. After recrystallisation the product melts at 115° C.

EXAMPLE 11

N-benzyl-N-(diethylphosphonomethyl)glycine of formula (X) (189 g) is dissolved in anhydrous tetrahydrofuran (600 ml). Triethylamine (60.6 g) is poured gradually into this first solution at ambient temperature. After 15 minutes the temperature is lowered from the ambient temperature to −10° C. and ethyl chloroformate (66 g) is poured gradually into the medium over 20 minutes. The temperature is then allowed to rise to +10° C. and the mixture is filtered; the precipitate is washed with tetrahydrofuran. The combined filtrates are evaporated.

The product of the formula:

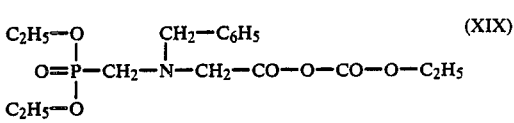

(225 g) is thus obtained.

This mixed anhydride is dissolved in $CH_2Cl_2$ (500 ml). Triethylbenzylammonium chloride (3 g) and N-methylmethane-sulphonamide (72 g) are added. The mixture is cooled to +10° C. An aqueous solution (51 g) containing 50% by weight of sodium hydroxide is then added dropwise. Stirring is continued for 1 h at 20° C.; water (300 ml) is added. After stirring the layers are separated; the organic phase is washed with water, dried and concentrated. An oily product of the formula (XII) (202 g; 83% yield), with a refractive index $n_D^{22}$ of 1.507 is obtained.

The various compounds of formula (I) shown in Table (I) are prepared by procedures according to examples 3, 4 and 11.

EXAMPLE 12

Herbicidal application during post-emergence of plant species

A number of seeds, determined depending on the plant species and the seed size, are sown in 9×9×9 cm pots filled with light agricultural soil.

The seeds are then covered with a layer of soil approximately 3 mm in thickness and each seed is left to germinate until it gives rise to a plantlet at the appropriate stage. The treatment stage for the graminaceous plants is the "second leaf being formed" stage. The treatment stage for the dicotyledon plants is the "cotyledons open, first true leaf being developed" stage.

The pots are then sprayed with a spraying mixture in a quantity corresponding to a volume application rate of 500 l/ha and containing the active ingredient at the required concentration.

The spraying mixture employed for the treatment is an aqueous suspension or solution of the active ingredient containing 0.1% by weight of Cemulsol NP 10 (surface-active agent consisting of polycondensate of ethylene oxide with an alkylphenol, particularly a polycondensate of ethylene oxide with nonylphenol) and 0.04% by weight of Tween 20 (a surface-active agent consisting of an oleate of a polycondensate of ethylene oxide derived from sorbitol).

The active ingredient was applied at the rate of 4 kg/ha.

The treated pots are next placed in troughs intended to receive the moistening water, by sub-irrigation, and maintained for 28 days at ambient temperature under 70% relative humidity.

At the end of 28 days, the number of living plants in the pots treated with the spraying mixture containing the active ingredient to be tested, and the number of living plants in a control pot treated under the same conditions but by means of a spraying mixture not containing active ingredient, are counted. The percentage destruction of the treated plants relative to the untreated control is thus determined. A destruction percentage equal to 100% shows that a complete destruction of the plant species in question has taken place and a percentage of 0% shows that the number of living plants in the treated pot is identical to that in the control pot.

The plants employed in the tests are:

| Abbreviation | Name | Latin Name |
|---|---|---|
| PA | Panic grass | *Echinochloa crus-galli* |
| RG | Italian ryegrass | *Lolium multiflorum* |
| BE | French bean | *Phaseolus vulgaris* |
| MU | Mustard | *Sinapis alba* |
| GO | Goosefoot | *Chenopodium album* |

The results obtained are shown in Table (II).

The compounds illustrated in Table (II) were also employed at a rate of 1 kg/ha and showed a good activity at this clearly lower rate; they also show a good activity on a large number of plants which are as diverse as those shown in Table (III).

The tests carried out thus show the remarkably advantageous properties of the compounds according to the invention, as herbicides with a wide activity spectrum and active during post-emergence; these products are in general inactive during pre-emergence.

When used in practice, the compounds according to the invention are most frequently used as part of compositions containing one or more other ingredients. These compositions, which can be employed as herbicidal agents, contain a compound according to the invention such as described earlier as the active ingredient in combination with the agriculturally acceptable solid or liquid carriers and surface-active agents which are also agriculturally acceptable. The inert and usual carriers and the usual surface-active agents can, in particular, be employed. Preferably, such herbicidal compositions contain as an active ingredient a compound of Formula I wherein $R^2$, $R^3$ and $R^4$ are all hydrogen and R is other than hydrogen and salts of such compounds. These compositions also form part of the invention.

These compositions may also contain all kinds of other ingredients such as, for example, protective colloids, adhesives, thickeners, thixotropic agents, penetrating agents, stabilizers, sequestering agents, or the like, as well as other known active ingredients with pesticidal properties (particulary insecticides, fungicides or herbicides) or with properties regulating the growth of plants. More generally, the compounds employed in the invention may be combined with all the solid or liquid additives corresponding to the usual techniques of formulation. For example, advantageous compositions include 0.1 to 7% ammonium salts, e.g., ammonium sulfate, and preferably 0.5 to 5% w/w.

The use doses of the compounds employed in the invention can vary within wide limits, particularly depending on the nature of the adventitious plants to be eliminated and the degree of infestation of the crops with these adventitious plants.

In the following, unless otherwise indicated, percentages are by weight.

In general, the compositions according to the invention usually contain approximately 0.05 to 95% (by weight) of one or more active ingredients according to the invention, approximately 1 to 95% of one or more solid or liquid carriers and, optionally, approximately 0.1 to 50% of one or more surface-active agents.

In accordance with what has already been stated the compounds employed in the invention are generally combined with carriers and, optionally, surface-active agents.

In the present account, the term "carrier" denotes an organic or inorganic ingredient, natural or synthetic, with which the active ingredient is combined to facilitate its application to the plant, to seeds or to the soil. This carrier is therefore generally inert and it must be agriculturally acceptable, particularly to the treated plant. The carrier may be solid (clays, natural or synthetic silicates, silica, resins, waxes, solid fertilizers, and the like) or liquid (water; alcohols, particularly butanol; esters, particularly methylglycol acetate; ketones, particularly cyclohexanone and isophorone; petroleum fractions; paraffinic or aromatic hydrocarbons, particularly xylenes; aliphatic chlorinated hydrocarbons, particularly trichloroethane, or aromatic chlorinated hydrocarbons, particularly chlorbenzenes; water-soluble solvents such as dimethylformamide, dimethyl sulphoxide, or N-methylpyrrolidone; liquefied gases, and the like).

The surface-active agent may be an emulsifying agent, dispersing agent or wetting agent of the ionic or non-ionic type or a mixture of such surface-active agents. There may be mentioned, e.g., salts of polyacrylic acids, salts of lignosulphonic acids, salts of phenolsulphonic or naphthalenesulphonic acids, polycondensates of ethylene oxide with fatty alcohols or fatty acids or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, and sulphate, sulphonate and phosphate functional derivatives of the above compounds. The presence of at least one surface-active agent is generally essential when the active ingredient and/or the inert carrier are only slightly water-soluble or are not water-soluble and the carrier in the composition is water.

For their application, the compounds of the formula (I) are therefore generally in the form of compositions; these compositions according to the invention are themselves in various solid or liquid forms.

Solid forms of compositions which can be mentioned are dusting powders (with a content of the compound of the formula (I) capable of ranging up to 80%) and granules, particularly those obtained by extrusion, compacting, impregnation of a granular carrier, or granulation starting from a powder (the content of the compound of the formula (I) in these granules being between 0.5 and 80% in these latter cases).

Solutions, in particular emulsifiable concentrates, emulsions, flowables, aerosols, wettable powders (or powder for spraying), dry flowables and pastes, can be mentioned as forms of compositions which are liquid or intended to form liquid compositions when applied.

The emulsifiable or soluble concentrates also comprise most frequently 5 to 80% of active ingredient, while the emulsions or solutions which are ready for application generally contain, 0.01 to 20% of active ingredient. Besides the solvent, the emulsifiable concentrates may contain, when required, 2 to 50% of suitable additives, such as stabilisers, surface-active agents, penetrating agents, corrosion inhibitors, colorants or adhesives.

Emulsions of any required concentration, which are particularly suitable for application to plants, may be obtained from these concentrates by dilution with water.

Examples 13 and 14 of the invention below are illustrations of some emulsifiable concentrates:

EXAMPLE 13

| | |
|---|---|
| Active ingredient | 100 g |
| polydcondensate of ethylene oxide and alkylphenol | 100 g |
| ethyleneglycol methyl ether | 400 g |
| aromatic petroleum cut distilling at between 160–185° C. | 400 g |

EXAMPLE 14

According to another formulation of emulsifiable concentrate use is made of:

| | |
|---|---|
| active ingredient | 50 g |
| epoxidized vegetable oil | 25 g |
| mixture of an alkylaryl sulphonate and a polyglycol ether and fatty alcohols | 100 g |
| dimethylformamide | 250 g |
| xylene | 575 g |

The concentrated suspensions, which can be applied by spraying, are prepared so as to produce a stable fluid product which does not settle (fine grinding) and usually contain from 10 to 75% of active ingredient, from 0.5 to 30% of surface-active agents, from 0.1 to 10% of thixotropic agents, from 0 to 30% of suitable additives such as anti-foaming agents, corrosion inhibitors, stabilizers, penetrating agents, adhesives and, as the carrier, water of an organic liquid in which the active ingredient is poorly soluble or insoluble; some organic solids or inorganic salts may be dissolved in the carrier to help prevent settling or as antifreezes for water, By way of example, below is an illustration of a flowable composition:

EXAMPLE 15

| | |
|---|---|
| Active ingredient | 500 g |
| phosphate of a polycondensate of ethylene oxide and tristyrylphenol | 50 g |
| polycondensate of ethylene oxide and an alkylphenol | 50 g |
| sodium polycarboxylate | 20 g |
| ethylene glycol | 50 g |
| organopolysiloxane oil (antifoam) | 1 g |
| polysaccharide | 1.5 g |
| water | 316.5 g |

The wettable powders (or powder for spraying) are usually prepared so that they contain 10 to 80% of active ingredient, and they usually contain, in addition to the solid carrier, from 0 to 5% of a wetting agent, from 3 to 10% of a dispersing agent and, when necessary, from 0 to 80% of one or more stabilisers and/or other additives such as penetrating agents, adhesives, or anti-caking agents, colorants, or the like. A particularly useful additive is ammonium sulfate. A solution for spraying can be formulated from a wettable powder by, for example, dissolving a composition of 80% w/w active ingredient and 20% w/w citric acid in water (less than 4 g/l) with one or more water soluble surfactants to form a diluted solution suitable for spraying.

Examples 16–22, below, are illustrations of some compositions of wettable powders in accordance with the invention:

EXAMPLE 16

| | |
|---|---|
| Active ingredient | 50% |
| calcium lignosulphonate (deflocculant) | 5% |
| isopropylnaphtahlene sulphonate (anionic wetting agent) | 1% |
| silica anti-caking agent | 5% |
| kaolin (filler) | 39% |

EXAMPLE 17

Another example of a wettable powder of 25% strength is given below:

| | |
|---|---|
| active ingredient | 25% |
| polycondensate of ethylene oxide and an aliphatic ($C_{10}$ to $C_{18}$) amine | 10% |
| polycondensate of ethylene oxide and an aliphatic ($C_8$ to $C_{18}$) alcohol | 10% |
| silica anti-caking agent | 25% |
| kaolin | 30% |

EXAMPLE 18

Another example of wettable powder is given below:

| | |
|---|---|
| active ingredient | 50% |
| sodium alkylnaphthalene sulphonate | 2% |
| methylcellulose of low viscosity | 2% |
| diatomaceous earth | 46% |

EXAMPLE 19

Another example of a wettable powder is given below:

| | |
|---|---|
| active ingredient | 90% |
| sodium dioctylsulphosuccinate | 0.2% |
| synthetic silica | 9.8% |

EXAMPLE 20

Another composition of a wettable powder of 40% strength employs the following components:

| | |
|---|---|
| active ingredient | 400 g |
| sodium lignosulphonate | 50 g |
| sodium dibutylnaphthalenesulphonate | 10 g |
| silica | 540 g |

EXAMPLE 21

Another composition of a wettable powder of 25% strength employs the following components:

| | |
|---|---|
| active ingredient | 250 g |

-continued

| | |
|---|---|
| isooctylphenoxy-polyoxyethylene-ethanol | 25 g |
| equal weight mixture of Champagne chalk and hydroxyethylcellulose | 17 g |
| sodium aluminosilicate | 543 g |
| kieselguhr | 165 g |

EXAMPLE 22

Another composition of a wettable powder of 10% strength employs the following components:

| | |
|---|---|
| active ingredient | 100 g |
| mixture of sodium salts of saturated fatty acid sulphates | 30 g |
| Product of condensation of naphthalenesulphonic acid with formaldehyde | 50 g |
| kaolin | 820 g |

To obtain these wettable powders, the active ingredient or ingredients is, or are, thoroughly mixed in suitable blenders with additional substances which may be impregnated on the porous filler and is, or are, ground using mills or other suitable grinders. This produces wettable powders the wettability and the suspendability of which are advantageous; they may be suspended in water to give any desired concentration and this suspension can be employed very advantageously in particular for application to plant foliage.

The "water dispersible granules (WG)" (granules which are readily dispersible in water) have a composition which is substantially close to that of the wettable powders. They may be prepared by granulation of formulations described for the wettable powders, either by a wet route (contacting finely divided active ingredient with the inert filler and a little water, e.g. 1 to 20%, or with an aqueous solution of dispersing agent or binder, followed by drying and screening), or by a dry route (compacting followed by grinding and screening). The solid granules can have a diameter, for example, from 0.25 to 1 mm. Additives, such as described for use in wettable powders, may be used with granules. In lieu of a solid support, a hydrophilic organic solvent such as a glycol derivative can be employed.

Formulations of water dispersible granules are illustrated in Examples 23 and 24:

EXAMPLE 23

| | |
|---|---|
| active ingredient | 800 g |
| sodium alkylnaphthalenesulphonate | 20 g |
| sodium methylene bis (naphthalene) sulphonate | 80 g |
| kaolin | 100 g |

EXAMPLE 24

| | | |
|---|---|---|
| active ingredient | 20% | w/w |
| surfactant(s) | 20-30% | w/w |
| citric acid | 4% | w/w |
| bentonite support | | |

As already stated, the aqueous dispersions and emulsions, e.g. compositions obtained by diluting with water a wettable powder of an emulsifiable concentrate according to the invention, are included in the general scope of compositions which may be employed in the present invention. The emulsions may be of the water-in-oil or oil-in-water type and they may have a thick consistency such as that of a "mayonnaise".

All of these aqueous dispersions of emulsions or spraying mixtures can be applied to the crops to be weeded, by any suitable means, chiefly by spraying, at the rates which are generally of the order of 100 to 1,200 liters of spraying mixture per hectare.

The compounds and compositions according to the invention are conveniently applied to vegetation and in particular to weeds to be eliminated when the latter have a green foliage. Preferably, such herbicidal compositions contain as an active ingredient a compound of Formula I wherein $R^2$, $R^3$ and $R^4$ are all hydrogen and R is other than hydrogen and salts of such compounds. Their persistence being low, it is possible to operate so that the crop is sown before or after treatment but emerges shortly after treatment (2 to 3 weeks) i.e. after the decompositions of the products of the invention.

The application dose of active ingredient is generally between 0.1 and 10 kg/ha, preferably between 0.5 and 8 kg/ha and most preferably between 1 and 4 kg/ha.

The principal function of the various additives or adjuvants referred to above is generally to facilitate the handling and the dispersion of the products according to the invention. In some cases, they may also assist the penetration of the active ingredient into the plant and may thereby increase the normal activity of the active ingredients according to the invention.

TABLE (I)

| | | | | | | Physical Properties | |
|---|---|---|---|---|---|---|---|
| Compound Number | R | $R^1$ | $R^2$ and $R^3$ | $R^4$ | m.p. in °C. | Refractive Index$_{20}$ $n_D$ | Other |
| 1 | $CH_3-$ | $CH_3-$ | $C_2H_5-$ | benzyl | | 1.507 | |
| 2 | $CH_3-$ | $C_2H_5-$ | $C_2H_5-$ | benzyl | | 1.506 | |
| 3 | $CH_3-$ | $(CH_3)_2CH-$ | $C_2H_5-$ | benzyl | | 1.504 | |
| 4 | $CH_3-$ | o-$CH_3-C_6H_4-$ | $C_2H_5-$ | benzyl | 146 | | |
| 5 | $CH_3-$ | p-$CH_3-C_6H_4-$ | $C_2H_5-$ | benzyl | | | I.R.: 1700 NMR: 3.30-3.92-11.5 |
| 6 | $C_2H_5-$ | $CH_3-$ | $C_2H_5-$ | benzyl | | 1.507 | |
| 7 | n-$C_3H_7-$ | $CH_3-$ | $C_2H_5-$ | benzyl | | | I.R.: 1696 |
| 8 | n-$C_4H_9-$ | $CH_3-$ | $C_2H_5-$ | benzyl | | 1.494 | |
| 9 | $CH_3-$ | $Cl-CH_2-$ | $C_2H_5-$ | benzyl | | 1.514 | |
| 10 | cyclopropyl | $CH_3-$ | $C_2H_5-$ | benzyl | | 1.505 | |
| 11 | $CH_3-$ | n-$C_4H_9-$ | $C_2H_5-$ | benzyl | | 1.491 | |
| 12 | $CH_3-$ | n-$C_3H_7-$ | $C_2H_5-$ | benzyl | | 1.499 | |

TABLE (I)-continued

| Compound Number | R | R¹ | R² and R³ | R⁴ | m.p. in °C. | Refractive Index₂₀ $n_D$ | Other |
|---|---|---|---|---|---|---|---|
| 13 | $CH_3-$ | $n-C_6H_{13}-$ | $C_2H_5-$ | benzyl | | 1.496 | |
| 14 | $CH_3-$ | $CF_3-$ | $C_2H_5-$ | benzyl | | 1.477 | |
| 15 | $CH_3-$ | $n-C_{12}H_{25}-$ | $C_2H_5-$ | benzyl | | 1.496 | |
| 16 | $CH_3-$ | $Cl-(CH_2)_3-$ | $C_2H_5-$ | benzyl | | 1.512 | |
| 17 | $C_6H_5-$ | $CH_3-$ | $C_2H_5-$ | benzyl | 95 | | |
| 18 | $n-C_6H_{13}-$ | $CH_3-$ | $C_2H_5-$ | benzyl | | | I.R.: 1700 |
| 19 | $CH_3-$ | $CH_3-$ | H | benzyl | 205 | | |
| 20 | $CH_3-$ | $C_2H_5-$ | H | benzyl | 212 | | |
| 21 | $CH_3-$ | $(CH_3)_2CH-$ | H | benzyl | 220 | | |
| 22 | $CH_3-$ | $o-CH_3-C_6H_4$ | H | benzyl | 205 | | |
| 23 | $CH_3-$ | $p-CH_3-C_6H_4$ | H | benzyl | 224 | | |
| 24 | $C_2H_5-$ | $CH_3-$ | H | benzyl | | | NMR: 3.74-4.72-13.2 |
| 25 | $n-C_3H_7-$ | $CH_3-$ | H | benzyl | | | I.R.: 1696 |
| 26 | $n-C_4H_9$ | $CH_3-$ | H | benzyl | | | NMR: 3.70-4.74-13 |
| 27 | $CH_3-$ | $Cl-CH_2-$ | H | benzyl | 155 | | |
| 28 | cyclopropyl | $CH_3-$ | H | benzyl | 222 | | |
| 29 | $CH_3-$ | $n-C_4H_9-$ | H | benzyl | 218 | | |
| 30 | $CH_3-$ | $n-C_3H_7-$ | H | benzyl | 217 | | |
| 31 | $CH_3-$ | $C_6H_{13}-$ | H | benzyl | 206 | | |
| 32 | $CH_3-$ | $CF_3-$ | H | benzyl | 150 | | |
| 33 | $CH_3-$ | $C_{12}H_{25}-$ | H | benzyl | 185 | | |
| 34 | $CH_3-$ | $Cl-(CH_2)_3-$ | H | benzyl | 202 | | |
| 35 | $C_6H_5-$ | $CH_3-$ | H | benzyl | 204 | | |
| 36 | $C_6H_{13}-$ | $CH_3-$ | H | benzyl | 221 | | |
| 37 | $CH_3-$ | $CH_3-$ | H | H | 213 | | |
| 38 | $CH_3-$ | $C_2H_5-$ | H | H | 219 | | |
| 39 | $CH_3-$ | $(CH_3)_2CH-$ | H | H | 232 | | |
| 40 | $CH_3-$ | $o-CH_3-C_6H_4-$ | H | H | 217 | | |
| 41 | $CH_3-$ | $p-CH_3C_6H_4-$ | H | H | 225 | | |
| 42 | $C_2H_5-$ | $CH_3-$ | H | H | 232 | | |
| 43 | $n-C_3H_7-$ | $CH_3-$ | H | H | 230 | | |
| 44 | $n-C_4H_9-$ | $CH_3-$ | H | H | 231 | | |
| 45 | $CH_3-$ | $Cl-CH_2-$ | H | H | 190 | | |
| 46 | cyclopropyl | $CH_3-$ | H | H | 235 | | |
| 47 | $CH_3-$ | $n-C_4H_9-$ | H | H | 236 | | |
| 48 | $CH_3-$ | $n-C_3H_7-$ | H | H | 230 | | |
| 49 | $CH_3-$ | $C_6H_{13}-$ | H | H | 240 | | |
| 50 | $CH_3-$ | $CF_3-$ | H | H | 180 | | |
| 51 | $CH_3-$ | $C_{12}H_{25}-$ | H | H | 230 | | |
| 52 | $CH_3-$ | $Cl-(CH_2)_3-$ | H | H | 213 | | |
| 53 | $C_6H_5-$ | $CH_3-$ | H | H | 234 | | |
| 54 | $C_6H_{13}-$ | $CH_3-$ | H | H | 237 | | |

TABLE (II)

| Compound No. | PA | RG | BE | MU | GO |
|---|---|---|---|---|---|
| 37 | 100 | 98 | 100 | 100 | 100 |
| 38 | 98 | 95 | 100 | 100 | 100 |
| 39 | 98 | 95 | 100 | 100 | 100 |
| 40 | 20 | 30 | 0 | 100 | 30 |
| 41 | 0 | 20 | 100 | 98 | 80 |
| 42 | 80 | 70 | 100 | 100 | 100 |
| 43 | 60 | 20 | 100 | 95 | 80 |
| 44 | 0 | 0 | 0 | 80 | 80 |
| 45 | 40 | 70 | 100 | 100 | 98 |
| 46 | 0 | 10 | 100 | 90 | 50 |
| 47 | 20 | 10 | 100 | 100 | 60 |
| 48 | 80 | 80 | 100 | 100 | 80 |
| 50 | 100 | 100 | 100 | 100 | 100 |
| 52 | 30 | 0 | 100 | 100 | 20 |
| 53 | 10 | 0 | 0 | 80 | 20 |

TABLE (III)

| English Name | American Name | Latin Name |
|---|---|---|
| Common amaranth | Pigweed | *Amaranthus retroflexus* |
| Indian mallow | Velvet leaf | *Abutilon theophrasti* |
| Prickly sida | Prickly soda | *Sida spinosa* |
| | | Sesbania |
| | Cocklebur | *Xanthium pennsylvanicum* |
| Black bindweed | | *Polygonum convolvulus* |
| Maize | Corn | *Zea mays* |
| Common chickweed | Chickweed | *Stellaria media* |
| Chrysanthemum | Corn marigold | Chrysanthemum |
| Hairy fingergrass | Crabgrass | *Digitaria sanguinalis* |
| | Giant foxtail | *Setaria faberi* |
| Black nightshade | | *Solanum nigrum* |
| | | *Cyperus esculentus* |

We claim:

1. A compound of the formula:

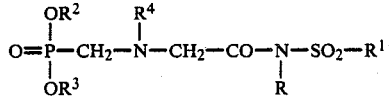

and the agriculturally acceptable salts thereof in which:
R¹ and R independently denote an alkyl radical of 1 to 7 carbon atoms, a cycloalkyl radical of 3 to 7 carbon atoms or a phenyl radical, said radicals being optionally substituted by chlorine or fluorine atoms; $R^2$, $R^3$ and $R^4$ denote the hydrogen atom.

2. A compound according to claim 1, in which $R^1$ is an alkyl radical of 1 to 7 carbon atoms.

3. A compound according to claim 1, in which $R^1$ is a cycloalkyl group containing from 3 to 7 carbon atoms.

4. A compound according to claim 1, in which $R^1$ is an alkyl group containing from 1 to 4 carbon atoms.

5. A compound according to claim 1, in which R is an unsubstituted alkyl radical containing from 1 to 4 carbon atoms and $R^1$ is an alkyl radical of 1 to 4 carbon atoms that is optionally substituted by chlorine or fluorine atoms.

6. A compound according to claim 1, in which R and $R^1$ are methyl groups.

7. A compound according to claim 1 which is in the salt form.

8. A compound which has the formula:

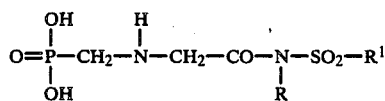

wherein R and $R^1$ are each alkyl groups having from 1 to 4 carbon atoms $R^1$ being optionally substituted by chlorine or fluorine, and the agriculturally acceptable salts thereof.

9. N-Methyl-N-methanesulphonyl-N-[N'-phosphonomethylglycyl]amine.

10. N-Methyl-N-ethanesulphonyl-N-[N'-phosphonomethylglycyl]amine.

11. N-Methyl-N-isopropanesulphonyl-N-[N'-phosphonomethylglycyl]amine.

12. N-Methanesulphonyl-N-[N'-benzyl-N'-diethylphosphonomethylglycyl]amine.

13. N-Methyl-N-methanesulphonyl-N-[N'-benzyl-N'-diethylphosphonomethylglycyl]amine.

14. N-Methyl-N-methanesulphonyl-N-[N'-benzyl-N'-phosphonomethylglycyl]amine.

15. A process for weeding, in which an effective dose of an active ingredient according to claim 1 is applied in contact with the leaves of the plants to be eliminated.

16. A process for weeding, in which a compound according to claim 1 is applied as an active ingredient at a rate of 0.1 to 10 kg/ha, preferably from 0.5 to 8 kg/ha.

17. A herbidical composition, which incorporates as an active ingredient a compound according to claim 1, this active ingredient being in association with at least one inert, conventional, agriculturally acceptable carrier.

18. A composition according to claim 17, which comprises 0.5 to 95% of active ingredient.

19. A composition according to claim 17, which comprises 5 to 40% of surface-active agent.

20. A composition according to claim 17, which is in the form of an emulsifiable concentrate.

21. A composition according to claim 17, which is in the form of a soluble powder or of a water-dispersible granule.

* * * * *